United States Patent [19]

Steiger et al.

[11] Patent Number: 5,275,063

[45] Date of Patent: Jan. 4, 1994

[54] MEASUREMENT OF HYDRATION BEHAVIOR OF GEOLOGIC MATERIALS

[75] Inventors: Ronald P. Steiger, Houston, Tex.; Rudolf J. Stankovich, Park City, Utah

[73] Assignee: Exxon Production Research Company, Houston, Tex.

[21] Appl. No.: 921,032

[22] Filed: Jul. 27, 1992

[51] Int. Cl.$^5$ .................................................. G01N 33/00
[52] U.S. Cl. ......................................... 73/865.6; 73/866
[58] Field of Search ....................... 73/152, 153, 37, 38, 73/865.6, 866

[56] References Cited

U.S. PATENT DOCUMENTS

| | | | |
|---|---|---|---|
| 2,612,036 | 9/1952 | Angona | 73/38 |
| 2,634,613 | 4/1953 | Napier | 73/38 |
| 2,703,977 | 3/1955 | Bailly | 73/38 |
| 2,705,418 | 4/1955 | Reichertz et al. | 73/38 |
| 2,737,804 | 3/1956 | Herzog | 73/38 |
| 3,139,747 | 7/1964 | Ferrell et al. | 73/38 |
| 3,199,341 | 8/1965 | Heuer, Jr. et al. | 73/820 |
| 3,216,242 | 11/1965 | Eyrich | 73/94 |
| 3,421,366 | 1/1969 | Ely | 73/819 |
| 3,423,994 | 1/1969 | Scott et al. | 73/819 |
| 3,423,995 | 1/1969 | Scott et al. | 73/819 |
| 3,457,777 | 7/1969 | Nielsen | 73/84 |
| 3,505,860 | 4/1970 | Bishop et al. | 73/819 |
| 3,610,032 | 10/1971 | Di Crispino | 73/819 |
| 3,616,685 | 11/1971 | Strom | 73/819 |
| 3,635,078 | 1/1972 | Wissa | 73/89 |
| 3,728,895 | 4/1973 | Shaw | 73/94 |
| 3,820,385 | 6/1974 | Cordoba | 73/84 |
| 3,881,345 | 5/1975 | Souder | 73/94 |
| 3,975,950 | 8/1976 | Erdef | 73/94 |
| 4,359,901 | 11/1982 | Bates et al. | 73/153 |
| 4,380,930 | 4/1983 | Podhrasky et al. | 73/594 |
| 4,430,890 | 2/1984 | Hains | 73/147 |
| 4,486,714 | 12/1984 | Davis, Jr. et al. | 324/376 |
| 4,487,056 | 12/1984 | Wiley | 73/38 |
| 4,502,338 | 3/1985 | Smith et al. | 73/819 |
| 4,506,542 | 3/1985 | Rose | 73/38 |
| 4,561,289 | 12/1985 | Jones | 73/38 |
| 4,562,726 | 1/1986 | Barnaby | 73/38 |
| 4,566,311 | 1/1986 | Barnaby | 73/19 |
| 4,579,003 | 4/1986 | Riley | 73/784 |
| 4,587,857 | 5/1986 | Bush | 73/863 |
| 4,599,891 | 7/1986 | Brauer et al. | 73/38 |
| 4,607,532 | 8/1986 | Arthur et al. | 73/819 |
| 4,625,544 | 12/1986 | Yuan et al. | 73/38 |
| 4,627,270 | 12/1986 | Jones | 73/38 |
| 4,631,677 | 12/1986 | Park et al. | 364/422 |
| 4,638,447 | 1/1987 | Odeh | 364/556 |
| 4,643,019 | 2/1987 | Jones | 73/38 |
| 4,648,261 | 3/1987 | Thompson et al. | 73/38 |
| 4,649,737 | 3/1987 | Jones | 73/38 |
| 4,669,299 | 6/1987 | Closmann | 73/38 |

(List continued on next page.)

FOREIGN PATENT DOCUMENTS

| | | | |
|---|---|---|---|
| 371877 | 6/1990 | European Pat. Off. | 73/38 |
| 252707 | 2/1970 | U.S.S.R. | 73/38 |
| 652266 | 3/1979 | U.S.S.R. | 73/38 |
| 700838 | 11/1979 | U.S.S.R. | 73/38 |
| 794434 | 1/1981 | U.S.S.R. | 73/38 |
| 815119 | 3/1981 | U.S.S.R. | |
| 1409894 | 7/1988 | U.S.S.R. | 73/38 |

OTHER PUBLICATIONS

"Quantitative Determination Of The Mechanical Properties Of Shales," Steiger and Leung, SPE Conference, Oct. 2-5, 1988.

(List continued on next page.)

Primary Examiner—Richard E. Chilcot, Jr.
Assistant Examiner—R. Biegel
Attorney, Agent, or Firm—Guy McClung

[57] ABSTRACT

Methods and apparatuses for testing the effects of one or more fluids on geologic materials; in one aspect a method for quantitatively determining the hydration and swelling behavior of shale core samples in response to one or to different fluids circulated around a core sample confined under pressure in a test cell; apparatuses for circulating such fluids and for conducting such tests; and an adjustable LVDT holder.

12 Claims, 7 Drawing Sheets

U.S. PATENT DOCUMENTS

| | | | |
|---|---|---|---|
| 4,679,421 | 7/1987 | Barree | 73/38 |
| 4,679,441 | 7/1987 | Johnson et al. | 73/798 |
| 4,710,948 | 12/1987 | Withjack | 378/208 |
| 4,715,212 | 12/1987 | Johanson | 73/38 |
| 4,753,107 | 6/1988 | Reed et al. | 73/38 |
| 4,762,003 | 8/1988 | Cioletti | 73/825 |
| 4,791,822 | 12/1988 | Penny | 73/865 |
| 4,799,382 | 1/1989 | Sprunt et al. | 73/153 |
| 4,807,465 | 2/1989 | Botzolakis et al. | 73/78 |
| 4,825,700 | 5/1989 | Vardoulakis et al. | 73/749 |
| 4,827,761 | 5/1989 | Vinegar et al. | 73/38 |
| 4,845,995 | 7/1989 | Kaste et al. | 73/794 |
| 4,848,145 | 7/1989 | Blaschke et al. | 73/153 |
| 4,856,341 | 8/1989 | Vinegar et al. | 73/798 |
| 4,864,846 | 9/1989 | Jones | 73/38 |
| 4,868,751 | 9/1989 | Dogru et al. | 364/422 |
| 4,876,512 | 10/1989 | Kroeger et al. | 324/376 |
| 4,879,654 | 11/1989 | Bruce | 364/422 |
| 4,884,438 | 12/1989 | Jones et al. | 73/153 |
| 4,885,941 | 12/1989 | Vardoulakis et al. | 73/794 |
| 4,955,237 | 9/1990 | Suzuki et al. | 73/784 |
| 4,957,001 | 9/1990 | Powell | 73/716 |
| 4,961,343 | 10/1990 | Boone | 73/152 |
| 5,018,396 | 5/1991 | Penny | 73/865.6 |
| 5,025,668 | 6/1991 | Sarda et al. | 73/795 |
| 5,025,669 | 6/1991 | Sarda et al. | 73/798 |
| 5,069,065 | 12/1991 | Sprunt et al. | 73/153 |
| 5,079,948 | 1/1992 | Collins et al. | 73/153 |

OTHER PUBLICATIONS

"Predictions Of Wellbore Stability In Shale Formations At Great Depth," Steiger and Leung, SPE Symposium 1989.

"Acoustical Properties Of Clay Bearing Rocks." C. A. Tosaya, 1982.

"Drilling Fluids,"0 Exxon Production Research Company, 1989.

"The Mechanics of Soils," Atkinson et al. 1978, pp. 118–144, 184–209, 292–343.

"Soil Merchanics," Lambe et al., 1969, Chapter 20, pp. 295–303.

"Lateral deformation gage for rock-mechanics testing," Schuler, 1978.

MEASUREMENT OF HYDRATION BEHAVIOR OF GEOLOGIC MATERIALS

BACKGROUND OF THE INVENTION

1. Field of the Invention

This invention is directed to the quantitative determination of properties of geologic materials and, in one aspect to the quantitative determination of the hydration behavior, including swelling stress and swelling pressure, of materials such as shales; and particularly the effect of different fluids on such materials.

2. Description of Related Art

Wellbores can become destabilized for a variety of chemical and mechanical reasons. A study of a sample core from a wellbore can reveal properties of the formation in which the well is located. These properties can indicate both chemical and mechanical causes of well destabilization and possible cures which will stabilize the wellbore. A variety of drilling fluids have been used to overcome destabilizing chemical mechanisms and mechanical mechanisms.

Shales are formations with high clay contents that are subject to hydration, swelling and reduction in compressive strength upon exposure to water. Shale formations make up a high percentage of the intervals drilled and cause most of the wellbore stability related problems. Confined shales upon exposure to low salinity water can develop very high swelling pressures. Inhibitive drilling fluids are often required to prevent wellbore destabilization due to shale hydration.

There is a great need for methods and apparatuses to accurately and quantitatively measure the hydration and swelling behavior of shales when exposed to different drilling fluids. Shales make up over 75% of drilled formations and often cause over 90% of wellbore stability problems and the associated stuck pipe. Choosing properly inhibitive drilling fluids for particular shales is a very difficult and uncertain task. The swelling pressure generated by a shale in the borehole wall upon exposure to a fluid has a great impact on the relative weakening of the shale and possible wellbore failure. Quantitative swelling pressures of preserved shales have not been measured in prior work.

SUMMARY OF THE PRESENT INVENTION

The present invention in one embodiment, discloses: a method for the quantitative evaluation of the effects of fluids on geologic materials, e. g., the effects of different chemicals such as inhibitive drilling fluids on low permeability rock such as shale; apparatus for making these determinations; and a single stage or a multistage method for sequentially testing a single sample of material to evaluate the effects on it of two or more fluids. In one particular embodiment a method is provided to quantitatively measure swelling pressures, swelling strain and hydrational behavior of preserved core shale samples upon exposure to one or several different chemicals or drilling fluids.

Prior measurement methods were directed to measuring certain properties of geologic materials, including strengths and pore pressures, using inert fluids. Methods according to the present invention are used to determine the effects of different chemical fluids on a sample by pumping and circulating the fluid around the sample and simultaneously measuring, e. g., the amount of swelling of the sample. A sensing system senses when a sample begins to swell and increases the confining pressure to compensate for such radial swelling. Preferably a sample is prepared so that the load of a load piston is applied perpendicularly to the bedding planes of the laminated layers of geologic material making up the sample and the greatest swelling pressure is therefore vertical, i.e., axial. An LVDT system is, preferably, used to sense axial increases in swelling pressure and to alert a load piston to move downwardly applying a greater load to compensate for these increases. The total swelling pressure is, therefore, a sum of the confining pressure plus the axial load.

In one embodiment of the present invention an integral preserved geologic core sample is maintained in a test cell under a confining pressure of, e.g., about five hundred p.s.i. while a test fluid, e.g. water or water with inhibitors, is circulated around the entire surface of the sample. It is preferred that the test fluid be circulated around the sample at a relatively low pressure, e.g. about 15 p.s.i. For samples having a great affinity for the test fluid, the sample will try to absorb the test fluid. Such absorbtion causes the sample to swell in both the axial and the radial directions. The least inhibitive fluid will cause the most swelling.

In one embodiment of the present invention triaxial swelling tests are performed on confined integral preserved shale cores to measure quantitatively the swelling pressures generated upon exposure to various drilling fluids. Carefully preserved shale cores are instrumented within a triaxial test cell and load frame to simulate downhole conditions. A single stage test of a single fluid on a core or a multistage test of multiple fluids on a core can be run. Multistage tests are run to determine the increase and decrease in swelling pressures generated by sequential exposure of several drilling fluids to one core. After exposure to a test fluid, the shale cores can be triaxially loaded to determine their compressive strengths. During a swelling test a computer data acquisition and control program is used to measure axial load, confining pressure, axial strain and transverse (radial) strains. Upon flowing a test solution such as water around a shale sample, preferably at very low pressure, the sample hydrates and swells, causing axial strain upward (i.e. negative axial strain) and causing radial strain outward (i.e. positive radial strain). In order to measure swelling pressure, it is preferred that no straining or relaxation of the sample is allowed. The computer, upon sensing infinitesimal strains, controls servo valves to a hydraulic pumping system to incease the isosttic confining pressure in the test cell (all around the core) to hold the radial dimensions constant and to control a load piston that provides axial load on the sample to maintain a constant core length. The sum of the confining pressure and the axial load on the core provides a measure of the swelling pressure developed upon exposure to a test fluid. After the sample has equilibrated at a swelling pressure for one test fluid, the test fluid pump can be stopped, the test fluid changed for another and the test pump can be restarted to circulate the new test fluid around the sample and to measure a new swelling pressure caused by the second fluid. Several fluids can be run in sequence on one core. For any test solution the load piston can be lifted from the sample to allow the sample to free swell in the axial direction, thus obtaining a measure of uniaxial swelling and obtaining a preserved hydrated core that then can be subsequently tested to failure in a triaxial strength test to measure the effects of hydration on its properties.

In one particular embodiment of this invention a strain measuring device is provided which has a body to which is mounted a flexible steel band for encircling a sample. A spring-loaded bolt is used to secure the band about a sample and a linear variable differential transformer (LVDT) connected to the bolt indicates dimensional change in the sample due to strain, thereby indicating the amount of circumferential strain.

Incorporated and included fully herein for all purposes are the disclosures of the following pending U.S. patent applications which are co-owned with this application:

U.S. application Ser. No. 07/577,337 filed on Aug. 31, 1990 entitled "Methods For Determining In Situ Shale Strengths, Elastic Properties, Pore Pressures, Formation Stresses and Drilling Fluid Parameters," naming Ronald P. Steiger and Peter K. Leung as co-inventors.

U.S. application Ser. No. 07/577,326 filed on Aug. 31, 1990 entitled "Methods and Apparatuses For Measurement Of The Strengths, Pore Pressures, And Mechanical Properties Of Low Permeability Geologic Materials," naming Ronald P. Steiger as inventor.

U.S. application Ser. No. 07/577,338 filed on Aug. 31, 1990 entitled "Microaccumulator For Measurement Of Fluid Volume Changes Under Pressure" naming Ronald P. Steiger, Peter K. Leung and Rudolf J. Stankovich as inventors.

U.S. application Ser. No. 07/576,692 filed on Aug. 31, 1990 entitled "Apparatuses And Methods For Adjusting A Material's Fluid Content And Effective Stresses," naming Ronald P. Steiger and Peter K. Leung as co-inventors.

U.S. application Ser. No. 07/576,697 filed on Aug. 31, 1990 entitled "Apparatuses And Methods For Measuring Ultrasonic Velocities In Materials," naming Ronald P. Steiger and Peter K. Leung as co-inventors.

U.S. application Ser. No. 07/671,367 filed on Mar. 19, 1991 entitled "Apparatuses And Methods For Measuring Ultrasonic Velocities In Materials," naming Ronald P. Steiger, Peter K. Leung and Rudolf J. Stankovich as inventors.

It is, therefore, an object of at least certain preferred embodiments of the present invention to provide:

New, useful, unique, efficient, and effective methods and devices for quantitatively measuring hydration and swelling properties of geologic materials;

Such methods for determining the effects of different chemicals, e.g. drilling fluids, on a geologic material such as low permeability rock, e. g. shale;

Such methods which permit multiple tests of different fluids to be run sequentially on a single sample of geologic material;

Such methods for quantitatively determining the swelling strain, swelling pressures, and hydrational behavior of shale wellbore samples in response to a variety of luids, inclduing but not limited to water and water containing shale inhibitors; and Devices for accurately measuring the strain on such samples; and for accurately testing such samples and making such measurements.

The present invention recognizes and addresses the previously-mentioned problems and long-felt needs and provides a solution to those problems and asatisfactory meeting of those needs in its various possible embodiments and equivalents thereof. To one of skill in this art who has the benefits of this inventions's realizations, teachings and disclosures, other and further objects and advantages will be clear, as well as others inherent therein, from the following description of presently-preferred embodiments, given for the purpose of disclosure, when taken in conjunction with the accompanying drawings. Although these descriptions are detailed to insujre adequancy and aid understanding, this is not intended to prejudice that purpose of a patent which is to claim an invention no matter how others may later disguise it by variations in form or additions of further improvements.

DESCRIPTIVE OF THE DRAWINGS

So that the manner in which the above-recited features, advantages and objects of the invention, as well as others which will become clear, are attained and can be understood in detail, more particular description of the invention briefly summarized above may be had by reference to certain embodiments thereof which are illustrated in the appended drawings, which drawings from a part of this specification. It is to be noted, however, that the description of certain preferred embodiments of the invention and is not to be considered limiting of its scope, for the invention may admit to other equally effective equivalent embodiments.

DESCRIPTION OF EMBODIMENTS PREFERRED AT THE TIME OF FILING FOR THIS PATENT

Figure 1:
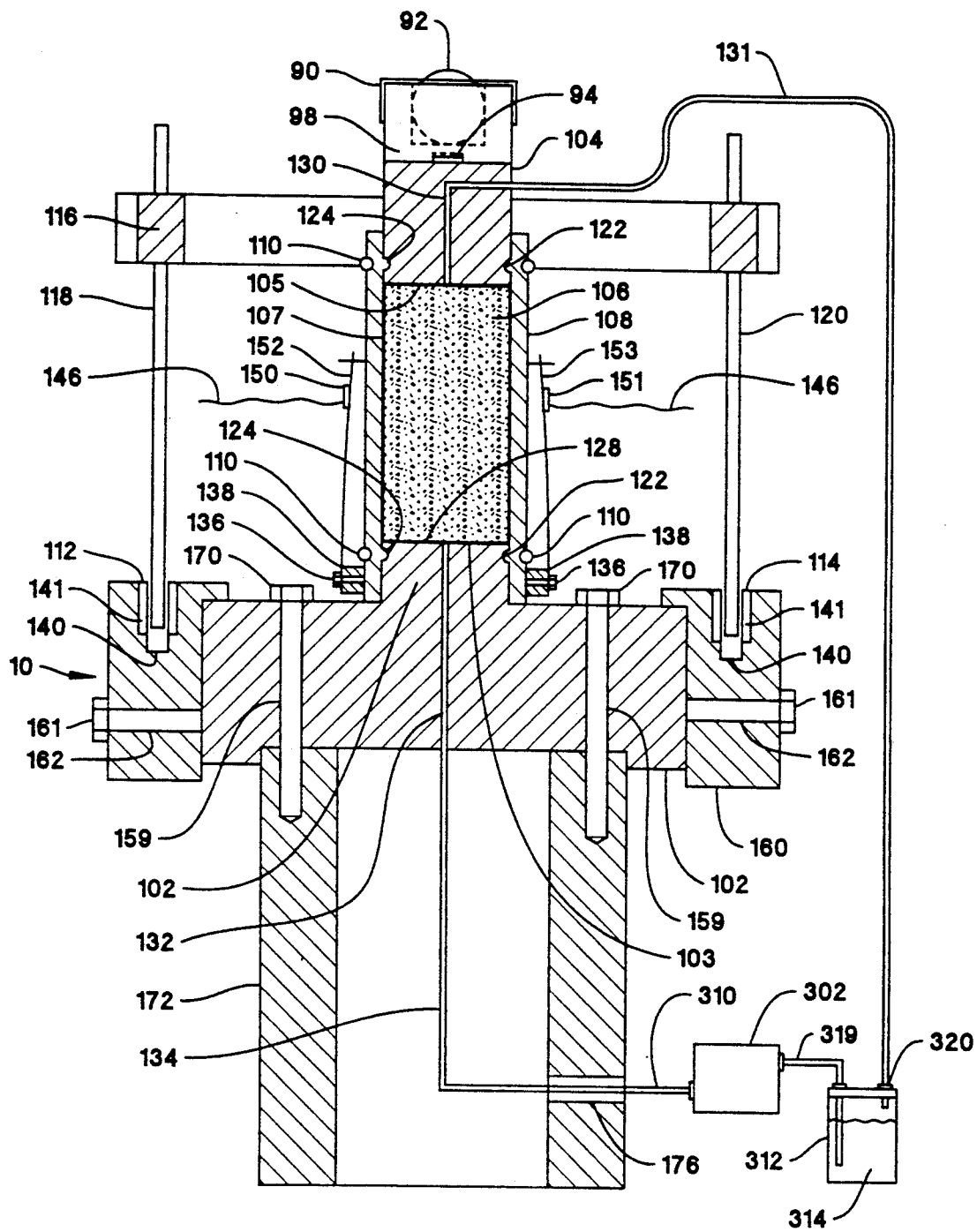
FIG. 1 is a side cross-section view of a test device according to the present invention.
Figure 3:
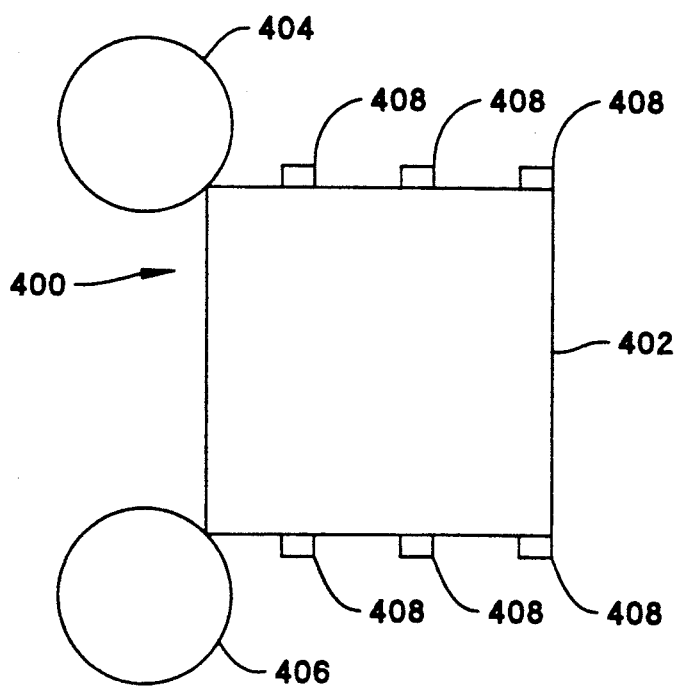
FIG. 3 is a plan view of a prior art sample screen device.
Figure 4:
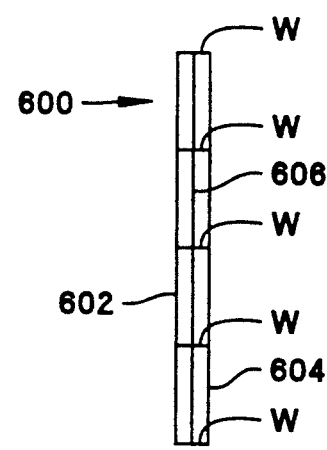
FIG. 4 is a side view of a prior art sample screen device.

Referring now to FIG. 1, an embodiment 10 of a test apparatus according to this invention has an instrumented load cell/top end cap/sample core/bottom end cap stack and an instrumented, preserved shale core 106 that is surrounded by a fine wire mesh screen 107 and enclosed in an impermeable plastic or rubber jacket 108. The fine wire mesh screen surrounding the shale core is made, preferably, from sandwiched multiple wire mesh layers, cut to fit the core, as shown in FIG. 3, spot welded together in layers as illustrated in FIG. 4 and then fitted around the sample prior to testing. The layered wire screens define a boundary which with the surface of the sample defines a conduit for circulating a test fluid around the sample during the test. The sample core is mounted between top 104 and bottom 102 triaxial end caps. Axial strain (change in core length) is measured by four linear variable differential transforemer (LVDT) assemblies (two whown, 118 and 120). Transverse or radial strains (radial swelling or shrinking of the core) are measured by two strain-gauged cantilever beam assembly (CBA) pairs configured orthogonal to each other and to a core axis. One CBA pair is illustrated by a CBA on the left 150,152,136 and a CBA on the right 151,153,136. The CBA's are mounted on a support ring 138, shown in FIG. 2, that is attached by screws 136 to the bottom end cap 102. (After the sample core of preserved shale is mounted, jacketed and instrumented, it is placed in a triaxial load frame test cell. The LVDT's, CBA's and load cell are connected to a computer and data acquisition system and a servocontrolled hydraulic pressure system as described in pending prior art U.S. application 07/577,326). A test fluid pump (for example a peristaltic pump) and test fluid chamber according to the present invention are connected to test inlet and exit tubes to provide a means to circulate test fluid (one test fluid or two or more different trst fluids sequentially) through the bottom end cap channel, around the test core sample, through the top end cap channel and back to the test fluid chamber.

During a swelling test according to this invention, the computer control program is used to measure axial load, confining pressure, axial strain and transverse strains. Upon flowing a test solution, such as water, around a shale sample, the sample hydrates and swells causing axial strain upward (i.e. negative axial strain) and causing radial strain outward (i.e. positive radial strain). In order to measure swelling pressure, it is preferred that no straining or relaxation of the sample be allowed. The computer, upon sensing infinitesimal strains, controls servovalves to a hydraulic pumping system to increase the isostatic confining pressure in the test cell (all around the core) to hold the radial dimensions constant and to a load piston that provides axial load on the sample to maintain a constant core length. The sum of the confining pressure and the axial load on the core provides a measure of the swelling pressure developed upon exposure to a test fluid. After the sample has equilibrated at a swelling pressure for one test fluid, the test fluid pump is stopped, the test fluid changed for another and the test pump is restarted to measure a new swelling pressure caused by sample uptake of the second fluid. Several fluids can be run in sequence on one core. For any test solution the load piston can be lifted from the sample to allow the sample to free swell in the axial direction, thus obtaining a measure of uniaxial swelling and obtaining a preserved hydrated core that then can be subsequently tested to failure in a traixial strength test to measure the effects of hydration on rock properties.

Figure 2:
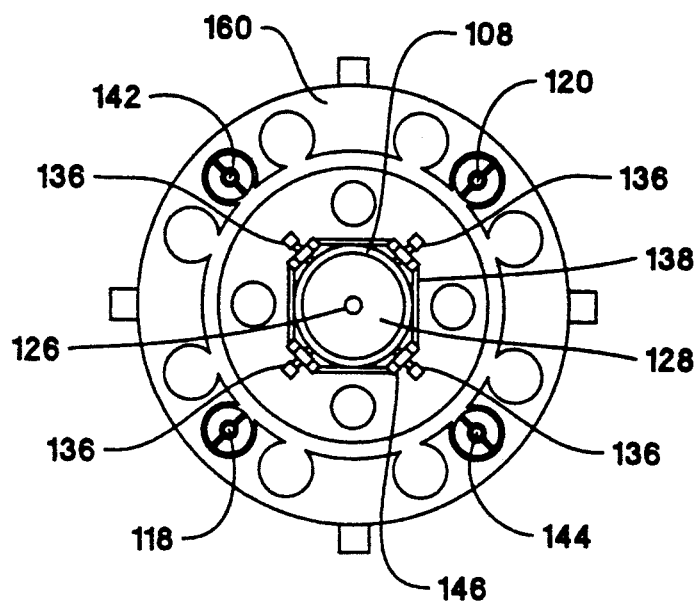
FIG. 2 is a top view of the device of FIG. 1.

As shown in FIGS. 1 and 2 a triaxial test cell apparatus 100 has the bottom end cap 102, and the top end cap 104. The core sample 106 is mounted on the bottom end cap 102 and beneath the top end cap 104. The flexible impermeable jacket 108 sheaths the sample 106 and extends slightly beyond it onto each end cap, and wire ropes 110 secure the jacket to the end caps so that an impermeable boundary is formed between the end caps and the sample. Lips 122 of the jacket 108 (or jackets if used) are received within corresponding grooves 124 in the end caps. A top screen 105 covers the top of the sample 106 and a bottom screen 103 which covers the bottom of the sample 106 lies on a top 128 of the bottom end cap 102. LVDT's 112 and 114 are disposed between the end caps and movably extend through holes 140 in a bottom collar 160 secured to the bottom end cap by set screws 161 through holes 162. LVDT rods 118 and 120 are secured to an LVDT holder 116 that is secured to the top end cap 104. The LVDT's (112, 114) indicate vertical movement of the end cap 104 due to axial movement (deformation) of the sample 106. The rods 118, 120 of the LVDt's are moveable in coils 141 in the bottom collar 160. A test fluid inlet tube 134 extends from the bottom end cap 102 to a pump 302. A test fluid channel 132 extends through the end cap 102 and communicates with the test fluid inlet tube 134. A test fluid outlet channel 130 extends through the top end cap 104 and is connected to a test fluid outlet tube 131 which itself is connected to an inlet 320 of a test fluid chamber 312.

Screws 136 secure a radial strain gauge ring 138 about the bottom end cap 102. Radial strain gauges indicate radial deformation of the test sample specimen. Cantilevered strain gauges 150, 151 are secured to arms 152, 153 which in turn are secured to the radial strain gauge ring 138. Wiring 146 is interconnected with and extends from the gauges 150, 151 (and others not shown) to the monitor/control computer. Holes 159 in the bottom of the end cap are for bolts 170 to mount the end cap to a bottom base 172. The apparatus 100 can be enclosed within a housing, not shown, and used with a piston, not shown and a pumping system, not shown. The pressure transducer 132 is a typical commercially available transducer ( e.g. Kulite Semiconductor Products, Inc. Model HEM 375-20000A), with a deflectable top portion with a strain gauge mounted thereon and wiring therefrom Test fluid 314 is pumped by a test fluid pump 302 from the test fluid chamber 312 to and through a test fluid conduit 310 extending through a hole 176 and which communicates with the test fluid inlet tube 134 from which fluid is pumped around the sample 106 and then out through the test fluid outlet channel 130 and the test fluid outlet tube 131 from which it is returned to the test fluid chamber 312 via the inlet 320.

As shown in FIG. 3, a screen member 400 for enclosing a sample to facilitate the flow of sample fluid therefrom has a main square portion 402 for encircling a side wall of a cylindrical sample and two circular portions 404, 406 connected thereto for folding over circular ends of a sample. Tabs 408 fold over the circular portions to provide further flow areas. As shown in 4, a screen 600 has three screen components 602, 604, and 606 spot welded together at points W. The screens may be of different mesh. In the particular embodiment shown, the screen 602 is 300 mesh and the screen 604 is 300 mesh. These relatively fine screens prevent the sample or the flexible jacket from entering the screen 606 which is of a coarser mesh, e.g. 100 mesh, thereby insuring that the screen 606 is not blocked and serves as a good flow path for test fluid.

Figure 8A:
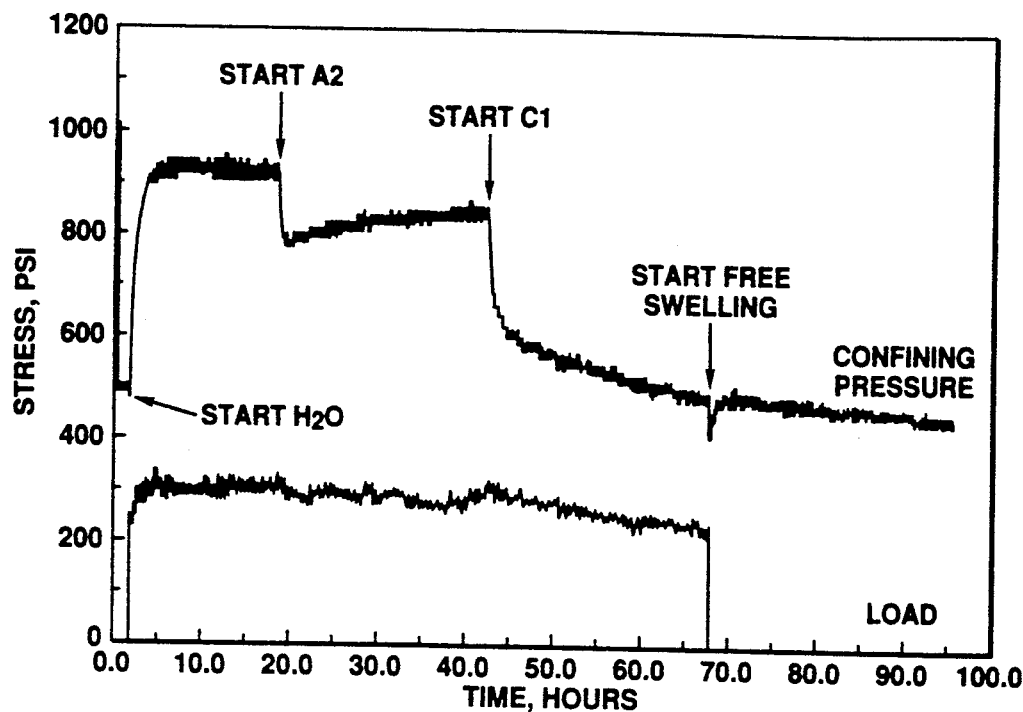
FIGS. 8A-8C are graphs that present test data from a method according to the present invention.

Test results from two tests are given in FIGS. 8A, B, C. As shown in FIGS. 8A, B, C, a preserved shale core was preloaded to a confining pressure of 1000 psi to seat the screens and jacket and then the confining pressure was reduced to 500 psi. The first test fluid, water, was pumped around the core. The sample started to hydrate and swell and the computer sensed the axial and radial strains and then increased the confining pressure and load from the piston to maintain the original sample dimensions. After an equilibrium period of about 16 hours the water test fluid was replaced with a slightly inhibitive test fluid A2 (which was 20% glycerol in water) and new pressures developed. The A2 test fluid was then replaced after 24 hours with a more inhibitive test fluid C1 (which was fluid A2 plus 28.5 grams/liter potassium chloride). After 24 hours the piston was lifted to allow the sample to free swell in the axial direction.

As shown in FIG. 8 at the start of the test (left side of the graph) water was circulated around the sample shale core and the sample attempted to swell. To counteract this swelling (and to measure it) the confining pressure, CP, was increased by the computer controlled sensing system to compensate for both radial and axial swelling of the sample. In this case the confining pressure was increased to about 940 p.s.i. The sample also attempted to swell further in the axial direction in opposition to the load piston. To compensate for this swelling the load, L, was increased to about 310 p.s.i. upon circulation of the A2 fluid around the sample (Start A2). The confining pressure initially decreased from its previous maximum and then climbed slightly, while the load remained about the same. Upon circulation of the C1 fluid around the sample (Start C1) the confining pressure dropped and the load tapered downward somewhat. To study free swelling of the sample, the load was released ("Start Free Swelling") and the confining pressure, which was slowly decreasing, was monitored.

Figure 8B:
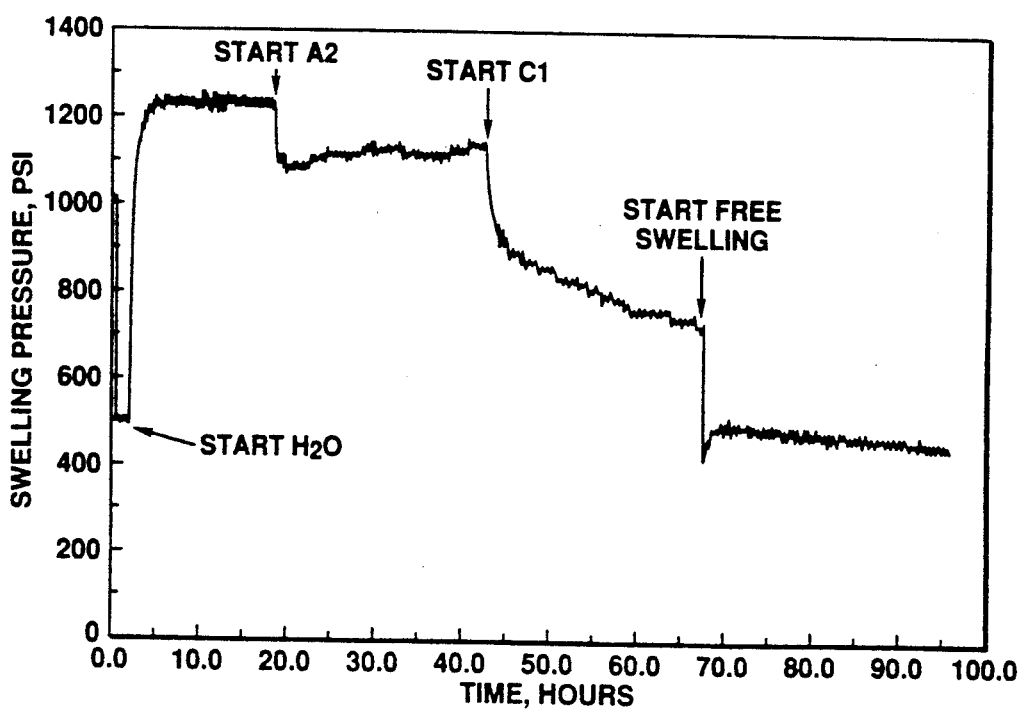
Figure 8C:
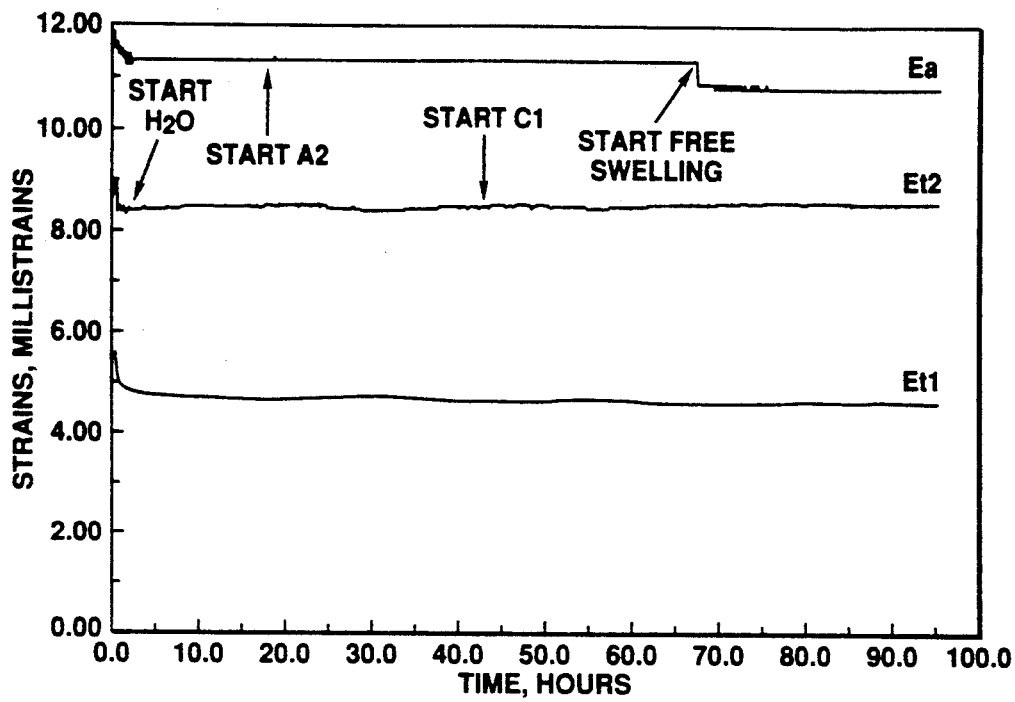

FIG. 8B presents data showing the total swelling pressure of the sample during the tests depicted in FIG. 8A. FIG. 8C presents the data obtained from the strain measuring devices on the sample during the tests depicted in FIG. 8A. Line Et 1 presents the data from the radial strain gauges on the side of the sample and line Et 2 presents the data from the cantilevers at right angles to the gauges shown on line Et 1. Line E A presents the average of the data obtained from the LVDT's for the axial strain. The computer, by increasing the confining pressure and axial load, maintained constant values for the radial dimensions shown by line Et1 and Et2 and the axial dimensions shown by line EA.

Figure 9A:
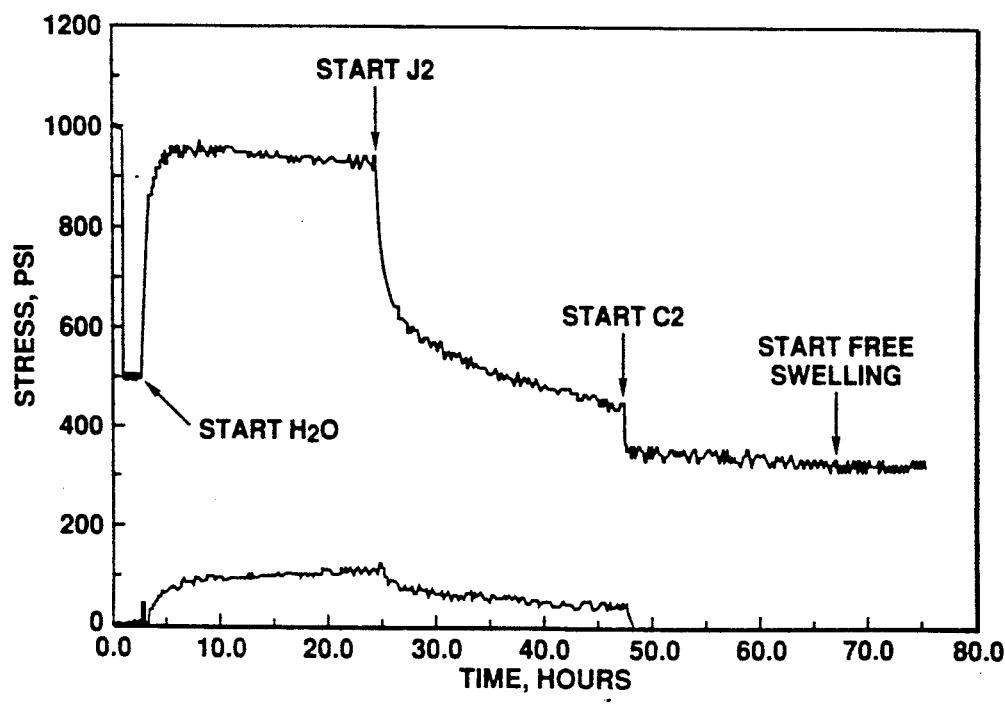
FIGS. 9A-9C are graphs that present test data from a method according to the present invention.
Figure 9B:
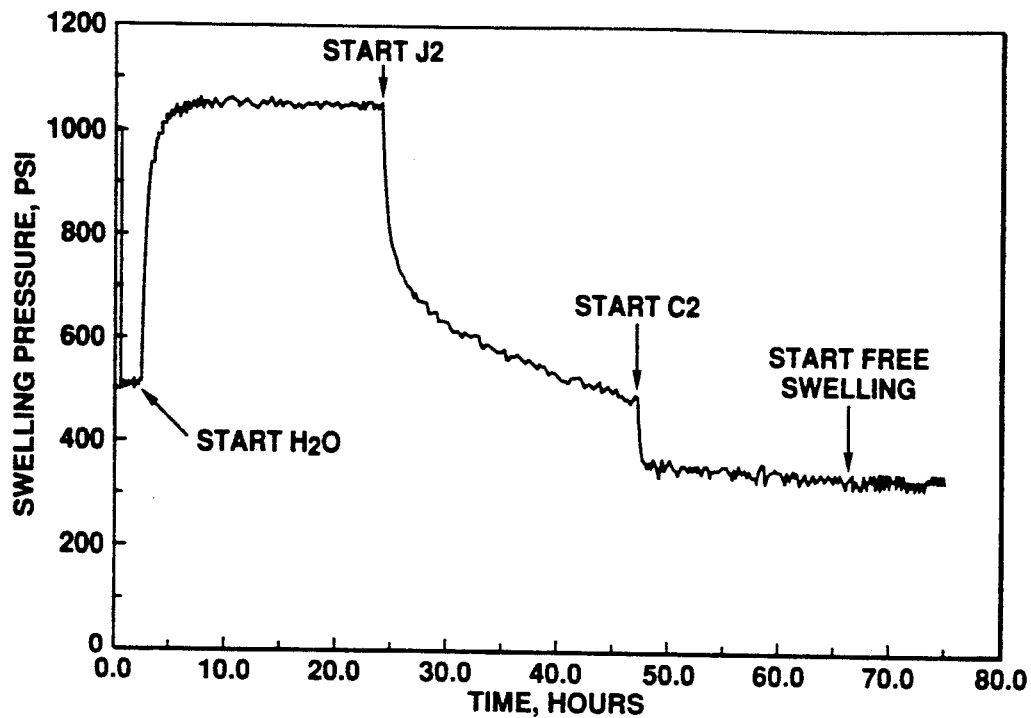
Figure 9C:
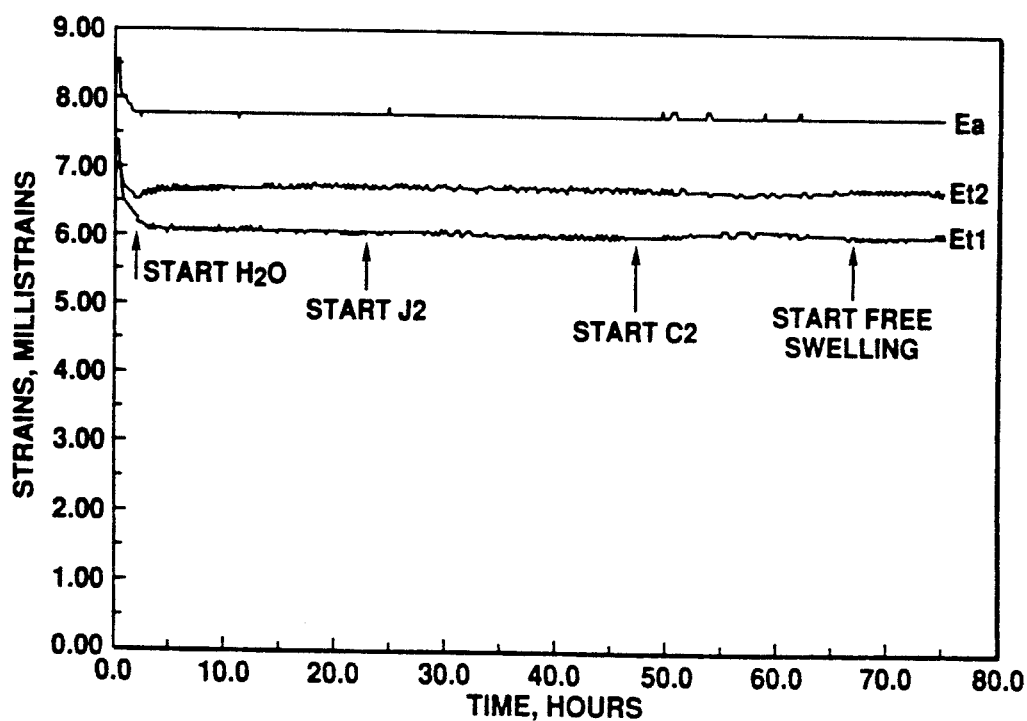

As shown in FIGS. 9A-9C a similar test was run with water, inhibitive fluid J 2 (which was a solution of 57 grams/liter potassium chloride in water) and a more inhibitive fluid C2 (which was solution J2 plus 20% glycerol) (fluids as described in pending U.S. application 07/641,415 filed Feb. 21, 1991 entitled "A Nontoxic, Nonchloride, Water-Base, Inhibitive Fluid To Stablize Water Sensitive Shales," incorporated herein in its entirety for all purposes and which is co-owned with the present invention and application).

Figure 5:
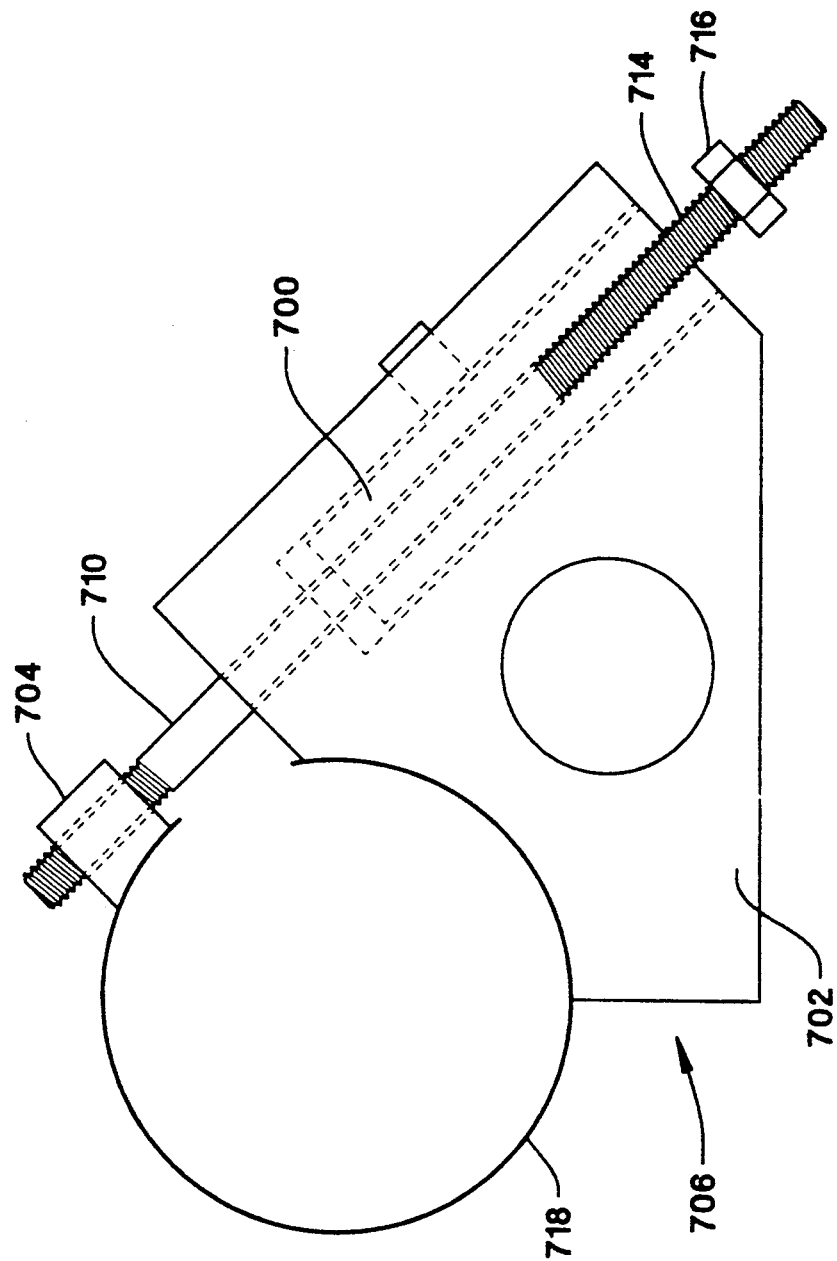
FIG. 5 is a top view of a strain measuring device according to the present invention.
Figure 6:
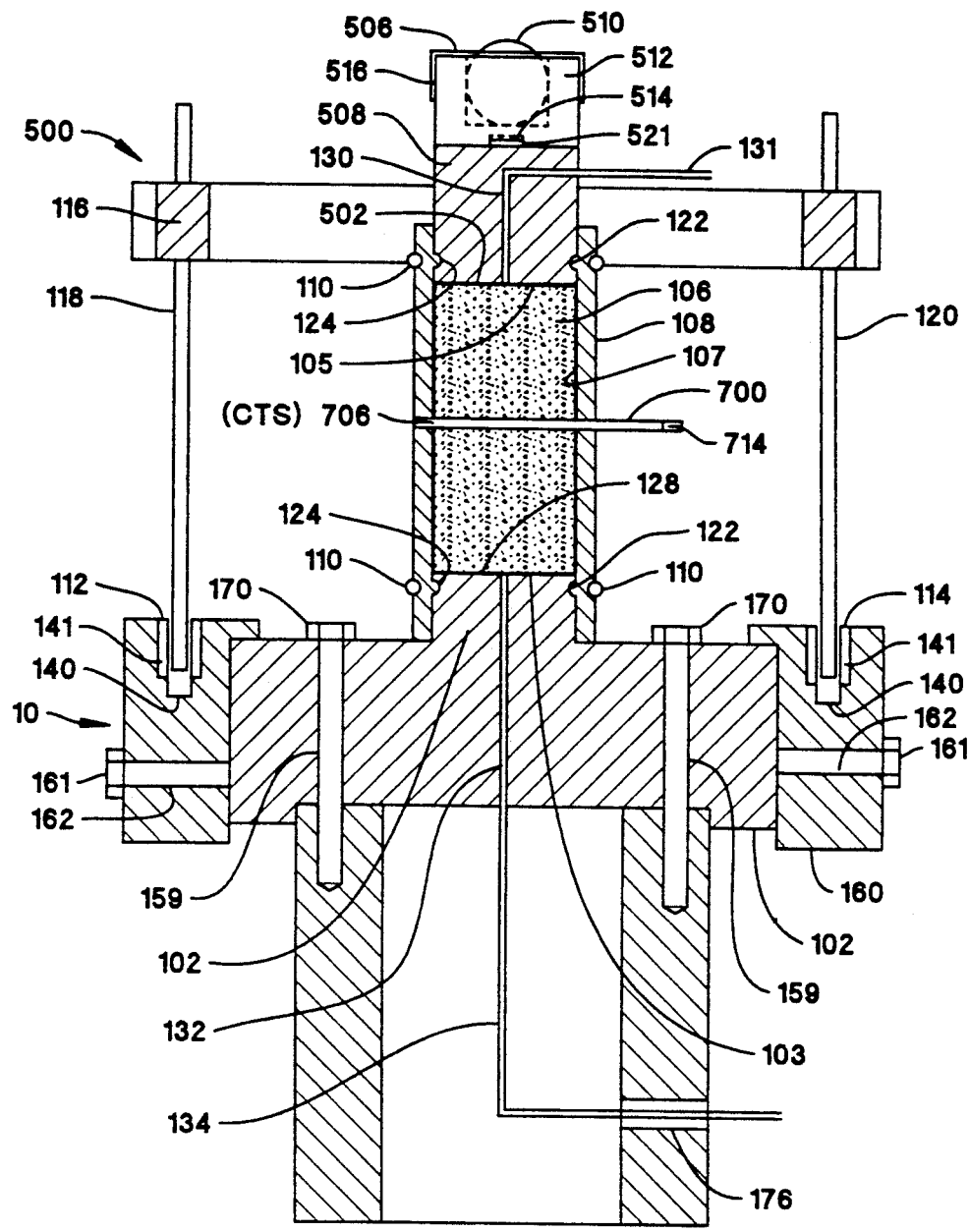
FIG. 6 is a side cross-section view of a test device according to the present invention with a strain measuring device as shown in FIG. 5.

A new circumferential transverse strain measuring device (CTS) 706 according to this invention is illustrated in FIG. 5. It has a steel band 718 that fits around a test core. Two metal ( e. g. aluminum) blocks are connected to each end of the band 718. One small block 704, an Lrod block, is designed to hold a threaded Lrod 710 and the large block 702, an LVDT holder block, is designed to hold a coil body 700 of a very sensitive, high output LVDT 720. The other end of the LVDT rod 710 is also threaded and extends through the LVDT coil body 700. A spring 714 is positioned on the rod between the LVD coil body 700 and a zeroing nut 716. The zeroing nut 716 can be adjusted in or out or hold the band 718 snug around a sample core and to zero position the LVDT rod 710 within the coil body 700. This CTS device 706 can be used as illustrated in FIG. 6 instead of the CBA's 152,153 illustrated in FIG. 1. The CTS device 706 measures circumference changes around the sample instead of only two orthogonal positions (as do the CBA's). It is thus more sensitive and provides better control of sample dimensions during a swelling test. The CTS device 706 also is useful for controlling sample dimensions during compression tests for critical state shale mechanics type measurements.

Figure 7:
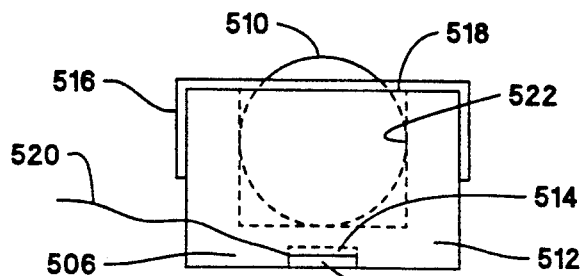
FIG. 7 is a side cross-section view of the top of the test device of FIG. 6.

A triaxial test apparatus 500 as shown in FIGS. 6 and 7 has a top load cell 506 mounted on a top end cap 502. The cell 506 has a self-centering steel ball 510 disposed partially within a recess 522 in a cylindrical steel frame 512. The ball 510 puts little or no torque on a sample to be tested and provides a relatively high stress at a center point of the frame 512, permitting sensitive accureate load measurement. A diapgragm strain gauge 514 is attached in a slot 521 in the bottom of the steel frame 512 at a point beneath the point at which the ball 510 contacts the frame 512. A load piston (not shown) contacts the ball 510 to impart a load through the top end cap 502 to a sample 106. A plastic cap 516 fits snugly over the frame 512 and has a hole 518 in its top through which the ball 510 protrudes. The cap prevents the ball from coming out of the frame 512. A typical conventional diaphragm gauge ( e.g. those provide by Micromeasurements Co.) may be used. Such gauges are accurate to about 2 to 10 psi in a load range of about 6000 to 8000 psi. The gauge's range can be increased to about 15,000 by changing the thickness of the frame around the slot to ( e.g. from 0.1 inch to 0.15 inch) and/or by using a diaphragm gauge with a higher range capability. Wiring 520 extends from the strain gauge 514 outside the test apparatus to a data acquisition and control computer as previously described. (Similar numbers in FIGS. 1 and 6 denote similar items.)

In conclusion, therefore, it is seen that the present invention and the embodiments disclosed herein and those covered by the appended claims are well adapted to carry out the objectives and obtain the ends set forth. Certain changes can be made in the described and in the claimed subject matter without departing from the spirit and the scope of this invention. It is realized that changes are possible within the scope of this invention and it is further intended that each element or step recited in ay of the following claims is to be understood as referring to all equivalent elements or steps. The following claims are intended to cover the invention as broadly as legally possible in whatever from its principles may be utilized.

What is claimed is:

1. A method for quantitatively measuring effects of fluids on a preserved sample of geologic material, the sample having an entire outer surface, the method comprising confining the sample under pressure in a test cell,
circulating a first test fluid around the entire outer surface of the sample, the sample changing dimensionally in three dimensions in response to the first test fluid,
controlling dimensional change in the sample and measuring dimensional change in the sample.

2. The method of claim 1 including the sample having original dimensions prior to confining the sample under pressure, and returning the sample to its original dimensions after the sample changes dimensionally.

3. The method of claim 1 wherein the sample has original dimensions prior to confining the sample under pressure, the method comprising also pumping the first test fluid away from the sample, circulating a second test fluid around the entire outer surface of the sample,
controlling dimensional change in the sample,
measuring dimensional change int he sample due to the second test fluid, and
returning the sample to its original dimensions.

4. The method of claim 1 wherein the sample has swelling pressure, the method comprising also pumping the first test fluid away from the sample, circulating a second test fluid around the entire outer surface of the sample, the sample's swelling pressure changing in response to the second test fluid, and measuring change in the sample's swelling pressure due to the second test fluid.

5. A method for quantitatively measuring effects of fluids on a preserved sample of geologic material, the sample having original dimensions, the sample having swelling pressure and an entire outer surface, the method comprising confinging the sample under pressure in a test cell, circulating a first test fluid around the entire outer surface of the sample, the sample developing a swelling pressure in response to the first test fluid, controlling dimensional change in the sample, and measuring the sample's swelling pressure.

6. The method of claim 5 including maintaining the sample's original dimensions after the sample develops a swelling pressure.

7. Test apparatus for measuring effects of fluids on preserved samples of geologic material, the apparatus comprising a test cell in which the sample is mountable and in which the sample can be subjected to pressure in three dimensions, means for circulating a first test fluid around the entire outer surface of the sample, the sample changing dimensionally in three dimensions in response to the first test fluid, means for controlling dimensional change of the sample, and means for measuring dimensional change of the sample in response to the first test fluid.

8. The test apparatus of claim 7 comprising also the sample has original dimensions prior to circulating a first test fluid around it, and means for returning the sample to its original dimensions after dimensional change of the sample.

9. The test apparatus of claim 7 comprising also means for pumping the first test fluid away from the sample and for pumping a second test fluid around the entire outer surface of the sample, the sample changing dimensionally in response to the second test fluid, and the means for measuring also for measuring dimensional change of the sample due to the second test fluid.

10. Test apparatus for measuring effects of fluids on preserved samples of geologic material, the sample having original dimensions and an entire outer surface, the apparatus comprising a test cell in which the sample is mountable and in which the sample can be subjected to pressure, means for circulating a first test fluid around the entire outer surface of the sample, the sample developing a swelling pressure in response to the first test fluid, means for controlling dimensional change of the sample and means for measuring the sample's swelling pressure in response to the first test fluid.

11. The test apparatus of claim 10 comprising also means for returning the sample to its original dimensions after change of the sample's swelling pressure.

12. The test apparatus of claim 10 comprising also means for pumping the first test fluid away from the sample and for pumping a second test fluid around the entire outer surface of the sample, the sample's swelling pressure changing in response to the second fluid, and the means for measuring also for measuring change of the sample's swelling pressure in response to the second test fluid.

* * * * *